(12) United States Patent
Bourlion et al.

(10) Patent No.: US 9,901,283 B2
(45) Date of Patent: *Feb. 27, 2018

(54) SYSTEM FOR THE CONSOLIDATION OF AN INDIVIDUAL'S BONE STRUCTURE, COMPRISING A SYSTEM FOR DETERMINING THE QUALITY OF THE BONE STRUCTURE

(75) Inventors: Maurice Bourlion, Rive de Gier (FR); Stéphane Bette, Corte Madera, CA (US)

(73) Assignee: LOUIS VUITTON MALLETIER, Paris (FR)

(*) Notice: Subject to any disclaimer, the term of this patent is extended or adjusted under 35 U.S.C. 154(b) by 111 days.

This patent is subject to a terminal disclaimer.

(21) Appl. No.: 13/883,924

(22) PCT Filed: Nov. 16, 2011

(86) PCT No.: PCT/FR2011/052652
§ 371 (c)(1),
(2), (4) Date: Jun. 4, 2013

(87) PCT Pub. No.: WO2012/066232
PCT Pub. Date: May 24, 2012

(65) Prior Publication Data
US 2013/0296734 A1 Nov. 7, 2013

(30) Foreign Application Priority Data
Nov. 16, 2010 (FR) ...................................... 10 59422

(51) Int. Cl.
*A61B 5/053* (2006.01)
*A61B 5/00* (2006.01)
(Continued)

(52) U.S. Cl.
CPC .......... *A61B 5/0538* (2013.01); *A61B 5/4504* (2013.01); *A61B 5/6878* (2013.01);
(Continued)

(58) Field of Classification Search
CPC ........................... A61B 5/0538; A61B 5/6878
See application file for complete search history.

(56) References Cited

U.S. PATENT DOCUMENTS 7,580,743 B2 * 8/2009 Bourlion et al. ............. 600/547
2006/0276721 A1 * 12/2006 McGinnis .................... 600/547

* cited by examiner

*Primary Examiner* — Daniel Cerioni
*Assistant Examiner* — Yasmeen S Warsi
(74) *Attorney, Agent, or Firm* — Miller, Matthias & Hull LLP (57) ABSTRACT

The invention relates to a system for the consolidation of a bone structure, comprising: a system for determining the quality of the bone structure, including a body, first and second electrodes arranged on the body, an electric generator for applying an electric current, a measurement device for measuring the electric current, and a processing device for determining an electrical magnitude representative of the aptitude of the bone structure for allowing electric current to pass therethrough and for delivering a signal representative of the quality of the bone structure, using the determined electrical magnitude; and a device selected from between an electrical stimulation device for applying an electric bone-growth stimulation and a fixation device for immobilizing the bone structure.

19 Claims, 7 Drawing Sheets (51) Int. Cl.
*A61B 17/64* (2006.01)
*A61B 17/88* (2006.01)
*A61N 1/08* (2006.01)
A61B 17/16 (2006.01)
A61B 17/66 (2006.01)
A61B 17/70 (2006.01)
A61B 17/00 (2006.01)
A61F 2/44 (2006.01)
A61F 2/30 (2006.01)
A61N 1/20 (2006.01)
A61N 1/32 (2006.01)
A61F 2/28 (2006.01)

(52) U.S. Cl.
CPC ...... *A61B 17/1671* (2013.01); *A61B 17/6491* (2013.01); *A61B 17/7082* (2013.01); *A61B 17/8883* (2013.01); *A61F 2/442* (2013.01); *A61N 1/08* (2013.01); A61B 5/053 (2013.01); A61B 17/1626 (2013.01); A61B 17/66 (2013.01); A61B 17/7007 (2013.01); A61B 17/7052 (2013.01); A61B 17/7092 (2013.01); A61B 2017/00022 (2013.01); A61F 2/4455 (2013.01); A61F 2002/2821 (2013.01); A61F 2002/30052 (2013.01); A61F 2002/30546 (2013.01); A61F 2002/30668 (2013.01); A61F 2002/448 (2013.01); A61F 2250/0001 (2013.01); A61N 1/205 (2013.01); A61N 1/326 (2013.01)

SYSTEM FOR THE CONSOLIDATION OF AN INDIVIDUAL'S BONE STRUCTURE, COMPRISING A SYSTEM FOR DETERMINING THE QUALITY OF THE BONE STRUCTURE

CROSS-REFERENCE TO RELATED APPLICATIONS

This application is a U.S. national stage filing under 35 USC § 371 of International Patent Application No. PCT/FR2011/052652 filed on Nov. 16, 2011, which claims priority under the Paris Convention and 35 USC § 119 to the French Patent Application No. 10 59422, filed on Nov. 16, 2010.

FIELD OF THE DISCLOSURE

The invention relates to a system for the consolidation of an individual's bone structure, comprising a system for determining the quality of the bone structure.

BACKGROUND OF THE DISCLOSURE

In the medical field, while performing surgery on a patient, the surgeon often operates on complex anatomical structures composed of multiple elements, for example on a bone structure, composed of a bone matrix which contains mineral elements and the bone marrow where blood cells are formed, or an intervertebral disc composed of a matrix of fibrous or gelatinous cartilage and water.

It is useful for the surgeon to be able to evaluate the quality of these structures objectively.

In particular, when the surgery on a bone structure consists of inserting an implant, for example a screw in a vertebra or a nail in a femur, the holding of this implant greatly depends on the quality of the anchorage and therefore on the quality of the bone structure into which it is inserted. An implant installed in a bone structure of poor quality, particularly porous bone, will not hold as well as the same implant installed in a bone structure of good quality.

After the operation, good anchorage of the implant is crucial to better union, to better fusion, and especially to decreasing the risks associated with poor anchorage of the implant in the bone structure, for example such as the onset of pain-generating pseudoarthrosis or the need for new surgery if implant migration occurs.

Also, with the aging of the general population, the trend is toward treating increasingly elderly patients who therefore have less solid bones. New implants are appearing on the market, such as expansion screws, dedicated for use in fragile bone not having bone structure of good quality. If the surgeon has objective knowledge of the quality of the bone structure he will be working with, he can adapt his therapeutic method accordingly. For example, for screw implantation in a vertebra, if the bone structure is not of good quality, he may decide to choose a screw of a larger diameter, or to use a specific implant, or to inject consolidating cement, or to treat an additional vertebra, or to use any other method he deems appropriate.

There are known techniques used prior to surgery that provide the surgeon with an indication of the bone structure quality.

For example, the DEXA method (Dual Energy X-ray Absorptiometry) allows measuring the bone density of different regions of the skeleton. This involves measuring the attenuation of two x-ray beams of different energy levels through tissues (soft and hard: organs and bones). Once the attenuation is known, the density of the traversed tissues is deduced using an attenuation equation according to the Beer-Lambert law. The examined areas may be the entire body or portions of it, specifically the spinal column, the hip, the neck of the femur, and the forearm (radius). The results of this examination are expressed as a score describing the measured bone mineral density in comparison to the corresponding normal value for the area in question. This examination allows evaluating the risk of fractures even before a first fracture appears. It is currently considered to be the standard for testing older women for osteoporosis.

Also known, from application WO 2008/119992, is a technique which first consists of applying and measuring alternating electrical signals emitted over a wide frequency range, within a portion of the body, then processing the electrical signals to determine the impedance and the phase shift for each of the frequencies and to use this to deduce a bone density value for that part of the body.

These non-invasive and painless techniques which are based on a rapid examination offering good results in terms of precision and reproducibility have the disadvantage, however, of providing a general examination which analyzes both the high-density cortical bone and the low-density cancellous bone.

As there may be a large variation within a bone structure in terms of quality (for example one vertebra may be of lesser quality than another neighboring vertebra in the same patient), knowing the general quality of the bone structure is insufficient. Local information is required.

To obtain local information on the quality of the bone structure, there is the known technique of bone biopsy, which consists of collecting a sample, generally under anesthesia, of a small bone fragment in order to analyze its structure. In principle, the biopsy location is the hip bone (iliac bone).

However, this technique has a certain number of disadvantages, including the need to expose the patient to an additional painful procedure and the inability to extrapolate this to the entire region where the surgeon is to work. In addition, obtaining information on the quality of the bone structure requires processing the collected fragment and is therefore not immediate.

Aside from the disadvantages mentioned above, the above techniques are pre-operative and increase the number and duration of the procedures the patient must undergo.

During surgery, however, it is critical that the operating time be as short as possible in order to decrease the risks (anesthesia, infection, etc.). As a result, the measurement of the local quality of the bone structure must be obtained without increasing the operating time.

Also known, from document U.S. Pat. No. 6,997,883, is a dental diagnostic system. The system comprises a body adapted for insertion into a preformed hole in the tooth, and a resistance measuring device comprising two electrodes for distinguishing healthy tooth tissue from diseased tooth tissue based on a difference in conductivity resulting from a difference from filling the tooth with liquid. This system, which applies to a tooth and not to a bone structure, requires drilling the tooth and filling the tooth with a liquid beforehand. In addition, the quality of the tissue is determined in a relative manner based on a variation in conductivity.

Document WO 2009/152244 describes a system for determining the depth of a hole in a bone structure, also comprising a body adapted for insertion into a preformed hole.

In the two systems mentioned above, the electrodes are in contact with tissue which is not the intact bone for which the quality is to be measured, but with a material resulting from mixing bone debris created from the prior drilling and the fluids that are present, for example blood. However, the resulting mixture does not have the same quality as the intact bone prior to drilling. As a result, these systems do not allow continuously determining the quality of a bone structure, particularly while during surgery or after surgery.

A need exists for a system for determining the quality of the bone structure which allows the surgeon to be able to evaluate the quality of this structure objectively, locally, and in real time during surgery but also after surgery, during the healing period.

SUMMARY OF THE DISCLOSURE

The invention proposes a consolidation system for a bone structure of a subject, comprising:
  a system for determining the quality of the bone structure, particularly the porosity of the bone structure, said system comprising:
    a body presenting an outside surface,
    at least one first electrode having a contact surface arranged on the outside surface of the body so as to come into contact with the bone structure,
    at least one second electrode having a contact surface arranged on the outside surface of the body so as to come into contact with the bone structure at a distance from the first electrode,
    an electric generator adapted for applying an electric current between the contact surfaces of the first and second electrodes for a determined period of time, said electric current having a characteristic chosen from among a voltage and an intensity which is known,
    a measuring device adapted for continuously measuring over the determined period of time the other characteristic chosen from among the voltage and the intensity of the electric current passing through the bone structure between the contact surfaces of the first and second electrodes, and
    a processing device adapted for continuously determining over the determined period of time an electrical magnitude representative of the capacity of the bone structure for allowing the passage of the electric current between the contact surfaces of the first and second electrodes, based on the known characteristic and on the measured characteristic, and for continuously delivering over the determined period of time a signal representative of the quality of the bone structure, particularly of the porosity of the bone structure, between the contact surfaces of the first and second electrodes, based on the determined electrical magnitude; et
  a fixation device adapted for immobilizing the bone structure so as to allow bone reconstruction, the fixation device being adapted for applying an adjustable mechanical load to the bone structure, in a manner that adjusts the mechanical load on the bone structure as a function of the signal representative of the quality of the bone structure, particularly of the porosity of the bone structure.

Thus, the invention allows measuring locally and continuously a magnitude representative of the capacity for allowing the passage of the electric current in order to deduce the quality of the structure from this in real time. This determination of the bone structure quality can be performed during surgery but also after surgery in order to monitor the bone reconstruction.

Indeed, the ability of a given material to allow the passage of electric current, represented in particular by the conductivity or resistivity of the material, is an intrinsic property of the material which depends on the nature of the material.

From a macroscopic point of view, the bone structure is a composite material primarily composed of two phases: solid bone which is a poor conductor, and bone marrow which contains conducting blood cells. Each of these two phases have distinct capacities for allowing the passage of electric current. The measurement of the general capacity of the bone structure for allowing the passage of electric current provides information on the proportion of these two phases and therefore on the quality of the bone structure. In a very hard bone structure such as cortical bone, the capacity for allowing the passage of electric current will be low because the poorly conducting solid phase is predominant, while the capacity for allowing the passage of electric current will be higher in osteoporotic bone given the higher presence of bone marrow, which is highly conductive.

Thus, the more the bone structure presents a high capacity for allowing the passage of electric current, the more porous the bone structure and the more it will be considered as being of poor quality.

In some arrangements, the system of the invention has advantageous applications in the field of fusion surgery (reconstruction), particularly for monitoring and confirming bone fusion. The invention can allow measuring the status of the bone fusion in order to follow-up the evolution.

Such follow-up is of great interest, as poor bone union can cause pain due to undesirable mobility that can lead to more surgery. Also, in order to maintain pressure on the bone during fusion, it is useful to be able to adapt the mobility, particularly by adjusting the rigidity of the implant (for example fusion plates or pins, devices with external fixators which are adjusted during fusion) or by adjusting or removing an orthosis (for example a supporting corset) or adjusting a functional reeducation program. It may be useful, when using stimulation of bone growth, to be able to adapt this stimulation to how the fusion is progressing.

Thus, with the invention, during the healing phase where the bone structures unify, the surgeon can check how the union is progressing in order to adapt his treatment (implant of variable rigidity, or stimulation of bone growth, adjustment and removal of the corset).

In one embodiment, the electric generator can be adapted for applying the electric current in the form of at least one electric pulse.

The processing device can be adapted for continuously calculating a value for the electrical magnitude during the determined period of time, and for continuously associating during the determined period of time the value calculated for the electrical magnitude with a value for the quality of the bone structure, particularly for the porosity of the bone structure.

Also, the processing device can be adapted for storing a transfer function relating each of the values in a range of values for the electrical magnitude to a value in a range of values for the quality of the bone structure, particularly for the porosity of the bone structure.

The processing device can be adapted for establishing a first ratio between the known characteristic and the measured characteristic, and for determining the electrical magnitude based on said first ratio.

In particular, it can be arranged so that the electrical magnitude is chosen from among the conductivity and the resistivity of the bone structure between the contact surfaces of the first and second electrodes, the processing device being adapted to:
- determine a distance between the contact surfaces of the first and second electrodes,
- determine dimensions of the contact surfaces of the first and second electrodes with the bone structure,
- establish a second ratio between said distance and said dimensions, and
- calculate the electrical magnitude based on the first and second ratios.

A low capacity for allowing the passage of electric current could then be characterized by a low conductivity or, conversely, by a high resistivity. A high capacity for allowing the passage of electric current could be characterized by a high conductivity or, conversely, by a low resistivity.

The processing device can be adapted for storing the distance between the contact surfaces of the first and second electrodes, and the dimensions of the contact surfaces of the first and second electrodes with the bone structure.

The contact surface of at least one of the first and second electrodes can have a dimension greater than 400 μm.

The processing device can be adapted for storing a set of values for the electrical magnitude over the determined period of time. Such an arrangement allows recording the evolution in the bone quality over the course of a measurement, for later processing.

In addition, the body can extend along a central axis to a distal end, with at least one of the first and second electrodes extending parallel to the central axis, the contact surface of said electrode being level with the outside surface of the body at the distal end.

At least one of the first and second electrodes can extend inside the body to a free end presenting the contact surface, said body comprising a layer of insulating material surrounding said electrode such that only said contact surface is level with the outside surface of the body.

The system as defined above may comprise a casing attached to the body and a power supply device supplying electrical energy to at least the electric generator and the measuring device, said casing being adapted to receive at least the electric generator, the measuring device and the power supply device.

In one embodiment, the casing forms a handle from which the body extends.

It can be arranged so that the casing and the body are attached together in a detachable manner, the body being made of a biocompatible material which can be implanted in the bone structure, the outside surface of the body being adapted to allow anchoring the body in the bone structure, the casing comprising means for electrically connecting the electric generator and the measuring device to the first and second electrodes.

The body can thus form an implant which improves the follow-up of the bone fusion. The casing, for example an external casing, meaning it is placed outside the patient, can ensure the application and measurement of the electric current while electrically connected to the implanted first and second electrodes.

In another embodiment, the casing and the body are made of a biocompatible material which can be implanted inside the subject.

In this embodiment, both the casing enclosing the components necessary for applying and measuring the electric current, and the body form an implant which in particular provides improved monitoring of the bone fusion.

Advantageously, the system may comprise a feedback loop in which the different components of the system are controlled as a function of the signal representative of the bone structure quality. This arrangement can be particularly useful in a system in which the body or the casing and body are implanted, to enable adjusting mechanical strains and/or electrical loads when electrical stimulation is being applied to the bone structure.

In particular, the consolidation system may further comprise an electrical stimulation device adapted for applying an electrical bone growth stimulation to the bone structure, the electrical stimulation device being adapted for applying an adjustable electrical stimulation to the bone structure, so as to adjust the electrical stimulation on the bone structure as a function of the signal representative of the quality of the bone structure, particularly of the porosity of the bone structure.

In order to provide the feedback loop, the processing device may be adapted for controlling the stimulation device as a function of the signal representative of the quality of the bone structure.

Besides, the stimulation device is composed of the electric generator and the first and second electrodes.

In order to provide the feedback loop, the processing device may be adapted for controlling the fixation device as a function of the signal representative of the quality of the bone structure.

Besides, the fixation device may comprise at least two fixation elements which can be implanted in the bone structure at a distance from one another, and a connecting element which connects the fixation elements, said connecting element having an adjustable rigidity.

In particular, the connecting element may comprise an elastic member exerting stress on the fixation elements, and a piezoelectric actuator arranged for adjusting the stress on the elastic member.

BRIEF DESCRIPTION OF THE DRAWINGS

Other features and advantages of the invention will be apparent from reading the following description of some specific embodiments of the invention, provided as non-limiting examples, with reference to the attached drawings in which.

DETAILED DESCRIPTION

In the figures, the same references are used to denote identical or similar items.

The figures represent a system 1 for determining the quality of a bone structure 2 in the body of a patient, intended to allow a surgeon to obtain local information in real time on the quality of the bone structure 2, and particularly on its porosity. As will be apparent in the rest of the description, this system 1 has advantageous applications not only during surgery on the bone structure 2, for example for placement of an implant, but also after surgery for following-up bone fusion, meaning reconstruction, and possibly for adapting the consolidation treatment to the progress in this reconstruction or adjusting a functional reeducation program. Although described in relation to an application in the body of a patient, the invention equally applies to determining the quality of the bone structure of the body in any other type of subject, particularly an animal or a cadaver.

In a first embodiment represented in FIGS. 1 to 6, the system 1 comprises a measuring instrument 5 and a central control unit 30.

Figure 2:
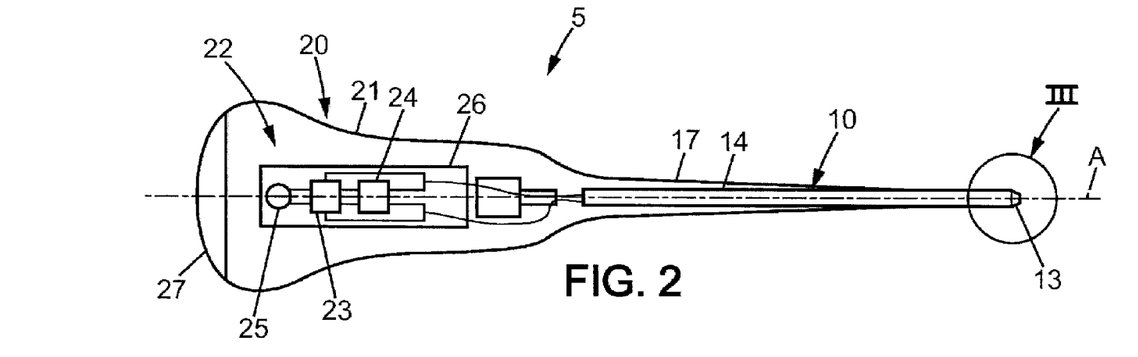
FIG. 2 is a representation of a measuring instrument being used in the system of FIG. 1, said measuring instrument comprising in particular a handle and a body.
Figure 3:
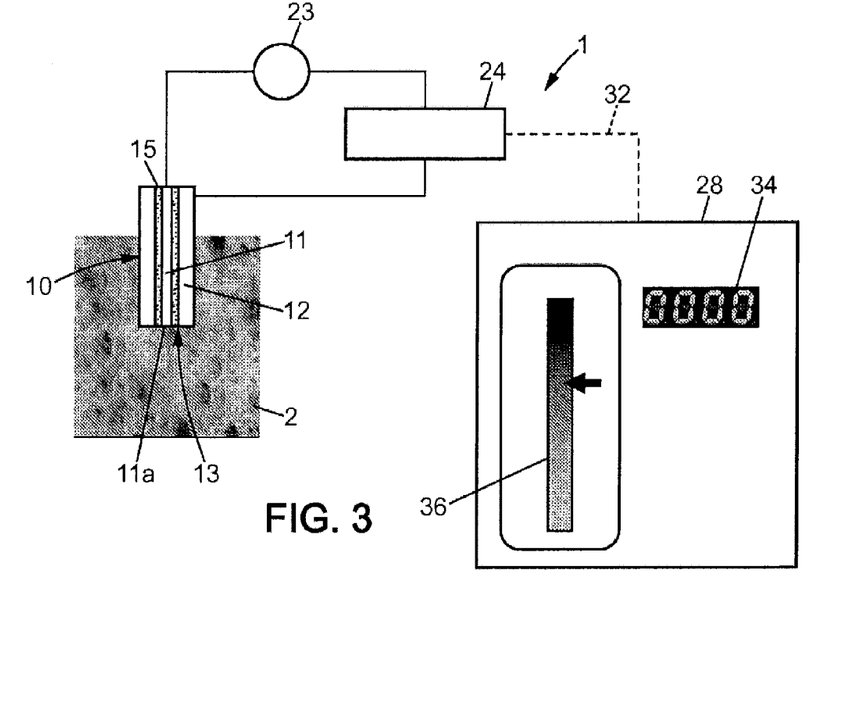
FIG. 3 is a schematic representation of the system of FIG. 1, illustrating the connection of first and second electrodes in a distal portion, denoted III in FIG. 2, of the body of the measuring instrument to an electric generator and a device for measuring electric current, a processing device providing a signal representative of the quality of the bone structure based on an electrical magnitude.
Figure 4:
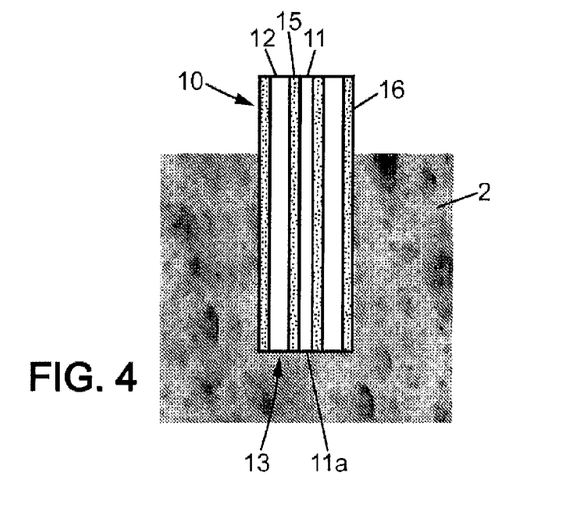
FIG. 4 is a schematic representation of a variant of the distal portion of the body of the measuring instrument of FIG. 2.

In FIGS. 2 and 3, the measuring instrument 5 is a hand-held tool, such as a tool for drilling the bone structure 2 of the type described in patent application WO 03/068076 and known by the name PediGuard®.

The measuring instrument 5 comprises a body 10 and a casing 20 forming a handle 21 that is attached to the body 10.

Although described in relation to a hand-held measuring instrument adapted for drilling in the bone structure 2, the invention is not limited to this type of instrument nor to its implementation as an instrument as it will appear in the rest of the description. In particular, the invention can be implemented in other types of instruments, particularly a probe, an awl, a paddle, a curette, or other instrument, or in an implant as described further below.

The body 10 has an outside surface 14 and serves to support first 11 and second 12 electrodes respectively presenting contact surfaces arranged to come into contact with the bone structure 2 at a distance from each other.

In the embodiment represented, the body 10, adapted for drilling in the bone structure 2, particularly a vertebral pedicle, is cylindrical along a central axis A with a circular cross-section and extends from the handle 21 to a distal end 13. The body could, however, be in any other form, particularly cylindrical having a polygonal or other cross-section.

As represented schematically in FIG. 3 which illustrates a distal portion of the body 10 near its distal end 13, the body 10 made of a conductive material is equipped with a central bore hole.

The first electrode 11 of conductive material is arranged in the central bore hole so that it extends inside the body 10 parallel and coaxial to the central axis A, out to a free end 11a presenting a contact surface level with the outside surface 14 of the body 10 at the distal end 13. A layer of insulating material 15 covers an inner surface of the central bore hole of the body 10 so that it surrounds the first electrode 11. In this manner, the first electrode 11 has a localized contact surface, meaning that only the contact surface of the first electrode 11 is level with the outside surface 14 of the body 12. To ensure the contact of the first electrode 11 with the bone structure 2, the dimension of the first electrode 11 is greater than that of the pore of the bone structure, which is generally between 100 and 400 μm.

The second electrode 12 is formed by the body 10 itself and presents a contact surface composed of a cylindrical portion parallel to the central axis A corresponding to a side surface of the body 10, and an annular portion generally perpendicular to the central axis A and corresponding to a distal surface of the body 10. The second electrode 12 is thus separated from the first electrode 11 by the layer of insulating material 15.

In this manner, the first electrode 11 presents a contact surface which is constant with respect to the bone structure to be investigated. Moreover, the first 11 and second 12 electrodes are placed on the body 10 at a fixed distance apart from each other.

The invention is not limited, however, to the embodiment and arrangement described above for the body and for the first 11 and second 12 electrodes. For example, in a variant represented in FIG. 4, the second electrode 12 is covered on a side surface parallel to the central axis A with a layer of insulating material 16, such that the contact surface of the second electrode 12 is limited to only the annular portion level with the outside surface 14 of the body 10 at the distal end 13. The body 10 can then be made of the insulating material, the first 11 and second 12 electrodes being fitted within the body 14.

More generally, the first 11 and second 12 electrodes are not necessarily arranged coaxially. In particular, these electrodes may each be realized as a pin inserted into the body 10. Moreover, the first electrode 11 and the second electrode 12 may each have a localized contact surface level with the side surface or the distal surface of the body, the second electrode 12 having, for example, a dimension greater than 400 μm. It may also be arranged so that the body supports two or more than two first electrodes 11 and two or more than two second electrodes 12.

The handle 21, cylindrical of revolution, extends substantially coaxially to the central axis A of the body 10. The shape of the handle 21 facilitates grasping and manipulating the instrument 5. The handle 21, made of plastic material, is attached to a sleeve 17 of plastic material extending over a portion of the outside surface 14 of the body 10.

The handle 21 comprises a housing 22 adapted for receiving an electric generator 23, a measuring device 24 and a power supply device 25 supplying electrical energy to the electric generator 23 and the measuring device 24. The electric generator 23, the measuring device 24 and the power supply device 25 are for example placed on a circuit board 26 inserted into the housing 22 through an opening provided at the end of the handle 21 opposite the body 10. A removable cap 27 closes the housing 22.

The first 11 and second 12 electrodes are electrically connected to the electric generator 23. The electric generator 23 is adapted to apply, for a determined period of time, an electric current between the contact surfaces of the first 11 and second 12 electrodes. The period of time in question can vary according to the application of the determination system. This is the period during which the quality of the bone structure must be determined; this period includes one or more measurements for determining one or more values corresponding to the quality of the bone structure as will be seen in the rest of the description. In particular, when applying the first embodiment to a measuring instrument, the period of time may correspond to the entire duration of the surgery or to a portion of it, and particularly to the duration of the drilling. When applied to an implant as mentioned above and described below in relation to a second embodiment of the invention, the period of time may correspond to the entire duration of the implantation in the body of the patient or to only a portion of this.

In particular, this concerns a voltage generator able to apply a voltage of known value or a current generator able to apply an electric current of known intensity.

Advantageously, to avoid polarization of the electrodes and therefore a loss of accuracy in the measurement by the measuring instrument 5, the electric generator 23 is adapted to apply the electric current in the form of an electric pulse or a series of multiple electric pulses. The electric pulses of voltage or current, for example all positive, respectively present determined intervals of time that are identical or different from one another. As a variant, the electric generator could deliver an alternating current, of any frequency. Although an electric current in the form of pulses or an alternating current are preferred, it is possible to have the electric generator 23 deliver a direct current.

In one particular example, the electric generator is a voltage generator delivering electric pulses at a voltage lower than 4 V in order to avoid nerve damage in case of contact, at a frequency lower than 10 Hz to allow muscle stimulation without fibrillation.

The measuring device 24 electrically connected to the first 11 and second 12 electrodes is adapted for continuously measuring, over the determined period of time during which the electric generator 23 applies the electric current:
  the voltage of the electric current passing through the bone structure 2 between the contact surfaces of the first 11 and second 12 electrodes, when the electric generator 23 is a current generator, or
  the intensity of the electric current passing through the bone structure 2 between the contact surfaces of the first 11 and second 12 electrodes, when the electric generator 23 is a voltage generator.

The measuring device 24 consists, for example, of an ammeter, a voltmeter, or any other device for measuring voltage or current (oscilloscope or dedicated circuit board).

In the particular example described, the measuring device measures the intensity of the electric current.

Thus, as represented in FIG. 3, during the drilling and penetration by the body 10 into the bone structure 2, the contact surfaces of the first 11 and second 12 electrodes are in contact with the bone structure 2. The known voltage is applied by the electric generator 23 between the contact surface of the first electrode 11, its dimension not varying during the penetration, and the contact surface of the second electrode 12 placed at a known distance from the first electrode 11. The intensity of the current circulating in the bone structure 2 between the contact surfaces of the first 11 and second 12 electrodes is measured. As indicated above, a current of known intensity can be applied and the voltage measured.

From the measurement obtained by the measuring instrument 5, an electrical magnitude representative of the capacity of the bone structure 2 for allowing the passage of the electric current can be determined and an indication of the quality of the bone structure 2 in contact with the first 11 and second 12 electrodes can be deduced.

Figure 1:
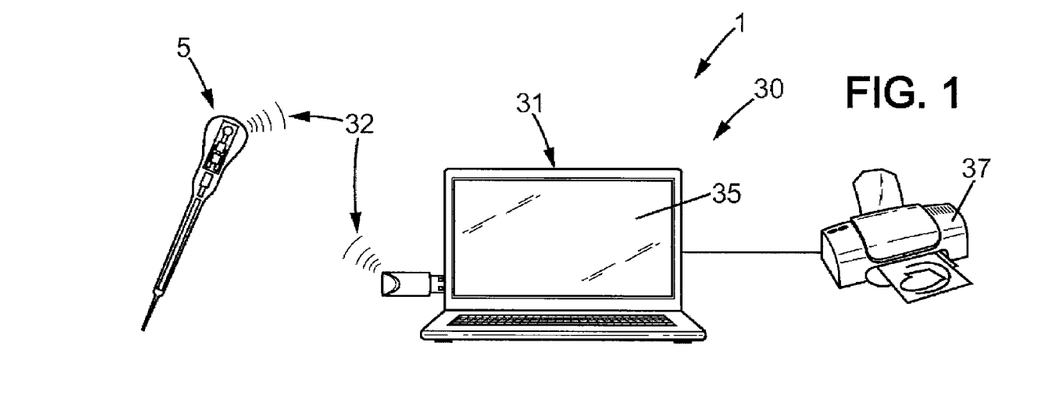
FIG. 1 is a representation of a system for determining the quality of a bone structure according to a first embodiment of the invention.

To do this, the measuring device 24 communicates by means of a communication interface 32, for example a remote interface as represented in FIGS. 1 and 3, with the central control unit 30 which comprises a processing device 28. The communication interface 32 may comprise a first transmitter/receiver placed in the measuring instrument 5, for example on the circuit board 26, and a second transmitter/receiver placed in a computer 31 constituting the central control unit 30. As a variant, the connection between the measuring instrument 5 and the central control unit 30 could be wired. It should be noted that the processing device 28 could be integrated with the measuring instrument 5, by placing it on the circuit board 26.

The processing device 28 is able to determine the aforementioned electrical magnitude continuously over the determined period of time, during which the voltage generator 23 applies the electric current at a known voltage and the measuring device 24 measures the intensity of the current passing through the bone structure between the contact surfaces of the first 11 and second 12 electrodes. In particular, the processing device 28 is adapted for continuously calculating a value for the electrical magnitude during the determined period of time, and for continuously associating during the determined period of time the value calculated for the electrical magnitude with a value for the quality of the bone structure 2, particularly the porosity of the bone structure 2. The processing device 28 is, moreover, adapted for continuously delivering during the determined period of time a signal representative of the quality of the bone structure, particularly the porosity of the bone structure 2, between the contact surfaces of the first 11 and second 12 electrodes based on the determined electrical magnitude.

In the specific example described, the electrical magnitude is the conductivity of the bone structure 2 between the contact surfaces of the first 11 and second 12 electrodes.

Indeed, the electrical conductivity is an intrinsic property of the material which depends on the nature of the material. As the bone structure 2 consists of two phases, poorly conducting solid bone and bone marrow containing conducting blood cells, having distinct electrical conductivities, measuring the electrical conductivity of the bone structure 2 provides information on the proportion of these two phases and therefore on the quality of the bone structure 2. Actually, in very hard bone such as cortical bone, the electrical conductivity will be low because the solid, poorly conductive phase will predominate, while the electrical conductivity will be higher in an osteoporotic bone given the higher presence of blood, a good conductor. Thus, the higher the electrical conductivity the lower the quality of the bone structure.

It is apparent from the above that the porosity representative of the proportion of each of the phases in the bone structure 2 constitutes an indicator of the quality of the bone structure 2. However, one can use other indicators of the quality of the bone structure 2, based on the proportion of each of the phases in the bone structure 2. For example, the proportion of bone mass M, with $M=1-P$ where P is the porosity of the bone structure, could serve as an indicator of the quality of the bone structure 2.

As indicated above, in order to measure the capacity of a material to allow the passage of current, the known voltage, in volts, is applied between the contact surfaces of the first 11 and second 12 electrodes in contact with the bone structure 2, and the resulting intensity, in amperes, is measured.

The processing device 28 can then establish a first ratio of the intensity, measured in this example, to the voltage, known in this example. This first ratio corresponds to the conductance measured in Siemens (S).

The electrical conductivity σ (in S/m), characteristic of the material being studied, is expressed as follows:

$$\sigma = \frac{L \times I}{A \times V}$$

where
I (in A) is the intensity of the electric current between the contact surfaces of the first 11 and second 12 electrodes, measured in this example but which could be known,
V (in V) is the voltage of the electric current between the contact surfaces of the first 11 and second 12 electrodes, known in this
L (in m) is the distance between the contact surfaces of the first 11 and second 12 electrodes;
A (in $m^2$) represents the dimensions of the contact surfaces of the first 11 and second 12 electrodes with the material.

The determination system could be integrated with any type of surgical instrument, of numerous configurations, particularly in terms of arrangement and geometry, where the first 11 and second 12 electrodes can be used. For each geometry, a calibration factor must be determined corresponding to a second ratio between the distance L between the contact surfaces of the first 11 and second 12 electrodes and the dimensions A of the contact surfaces of the first 11 and second 12 electrodes with the bone structure.

When, as in the present case, the contact surfaces of the first 11 and second 12 electrodes do not have the same dimensions, the value taken into account for the dimension A of the contact surfaces of the first 11 and second 12 electrodes with the material is the dimension of the smallest contact surface. As the contact surface of the second electrode 12 increases with the penetration of the measuring instrument, the smallest contact surface to be taken into account is that of the first electrode 11, which remains constant during the penetration.

Thus, in the embodiment represented, knowing the arrangement and geometry of the contact surfaces of the first 11 and second 12 electrodes, the calibration can be conducted during the design of the measuring instrument 5 and the calibration factor determined once and for all. To do this, the first ratio between the intensity and the voltage will be measured for a known bone quality and, as the electrical conductivity of the conducting phase is known, the calibration factor can be deduced from this. In particular, it is sufficient to measure the conductance value in the conducting phase of the bone structure (blood) and say that this corresponds to 100% porosity. For the insulating phase of the bone structure (solid bone), the conductance is 0 for a porosity of 0%.

The processing device 28 may include memory in which is stored the calibration factor and/or the distance L between the contact surfaces of the first 11 and second 12 electrodes and the dimensions A of the contact surfaces of the first 11 and second 12 electrodes with the bone structure. The user of the measuring instrument 5 then no longer needs to concern himself with this aspect. In the embodiment represented, the calibration factor is within the range of 380-500 $m/m^2$.

The system described above, in which the calibration factor is stored, therefore allows measuring the electrical conductivity of the bone structure 2 based on a single intensity (or voltage) measurement.

As a variant, when the contact surfaces of the first 11 and second 12 electrodes both vary, it is possible to adapt the processing device 28 to:
determine the distance L between the contact surfaces of the first 11 and second 12 electrodes,
determine the dimensions A of the contact surfaces of the first 11 and second 12 electrodes with the bone structure 2, and
establish the calibration factor.

As is apparent from the above description, for a same arrangement and a same geometry of the contact surfaces of the first 11 and second 12 electrodes, the conductance can be directly representative of the quality of the bone structure.

Figure 5:
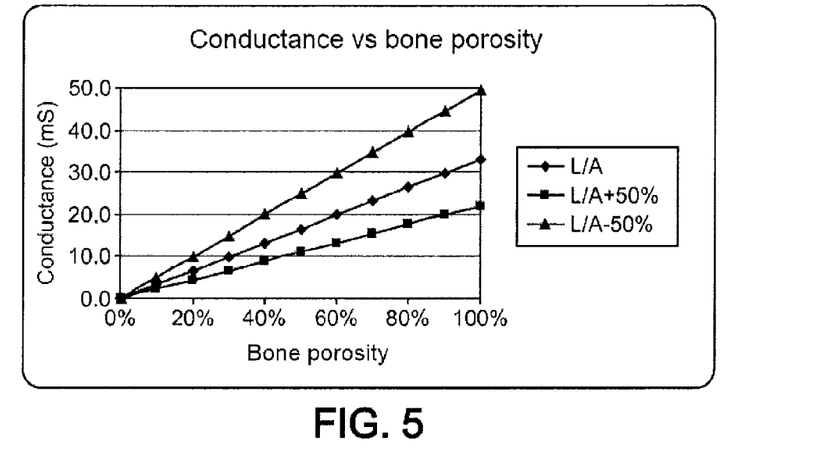
FIG. 5 is a graph illustrating a transfer function relating the electrical conductance to the bone porosity for different configurations of the first and second electrodes.

In FIG. 5, a transfer function relating the conductance to the porosity of the bone structure is represented. In particular, the transfer function relates each of the values within a range of conductance values to a value within a range of porosity values. Such a transfer function is stored in the memory of the processing device 28.

The transfer function, for example substantially a linear function, can be obtained by calibration in a conducting medium and an insulating medium, respectively providing the extreme values for the electrical magnitude. The extreme values for the electrical magnitude then correspond to the extreme values for the porosity of the bone structure. The extreme values for the electrical magnitude define the range of values for the electrical magnitude within which each electrical magnitude value corresponds to a bone structure porosity value.

For the measuring instrument represented, the measurement range of the first voltage and intensity ratio is between 3000 and 10 KΩ in terms of impedance (ratio V/I) for bones in the spinal column, and between $1 \times 10^{-4}$ S and $3.3 \times 10^{-3}$ S in terms of conductance (ratio I/V) for bone qualities ranging from very hard cortical bone to blood (case where there is almost no remaining bone structure).

The graph of FIG. 5 represents the relationship between the conductance measurement and the bone porosity obtained with the factor L/A, corresponding to the arrangement and geometry of the measuring instrument 5 as described above. The curves obtained with a calibration factor L/A 50% larger and a calibration factor L/A 50% smaller than what was described above have been added to this graph. The values on the x axis are given as a % porosity of the bone structure, which corresponds to the amount of blood present in the bone structure (0% being a completely insulating material and 100% being the measurement obtained in pure blood).

The description just provided for a processing device 28 that processes the conductance measurement and determines the conductivity of the bone structure is directly transposable to a processing device 28 that processes the impedance measurement and determines the resistivity of the bone structure.

Thus, in the determination system of the invention, as soon as an intensity (respectively a voltage) is measured, the voltage (respectively the intensity) being known, the value of the conductance (respectively the impedance) is determined. This conductance (respectively impedance) value corresponds, directly or indirectly via the calibration factor which allows obtaining the value of the conductivity (respectively the resistivity), to the value of the porosity of the bone structure 2 and therefore to a value reflecting its quality.

The processing device 28 can deliver continuously, during the determined period of time, the signal representative of the quality of the bone structure between the contact surfaces of the first and second electrodes.

This signal may be of any appropriate type: electrical, visual, auditory, or other. In particular, it may be an electrical signal communicated to the central control unit 30 for later processing. The processing device 28 may also comprise a result indicator for the quality of the bone structure. The result indicator can be in the form of any device which gives a visual indication of the quality of the bone structure. In particular, the result indicator, such as a display 34, a computer screen 35, a galvanometer, a light graduated scale 36, for example an LED light strip, or other, allows reading the value determined for the bone structure quality. In addition or as an alternative to the visual indication specified above, the result indicator could provide an audible indication. The processing device 28 may be connected to a device for saving and/or documenting the results obtained, which in the embodiment represented is in the form of a digital record, particularly on the hard drive of the computer 31, and a printer 37, in order to give a specialist the possibility of making a diagnosis.

Aside from the instantaneous indication of the local quality of the bone structure, it can be arranged to record, for example in the memory of the processing device 28, all values representative of the bone structure quality during the pre-determined period of time.

Figure 6A:
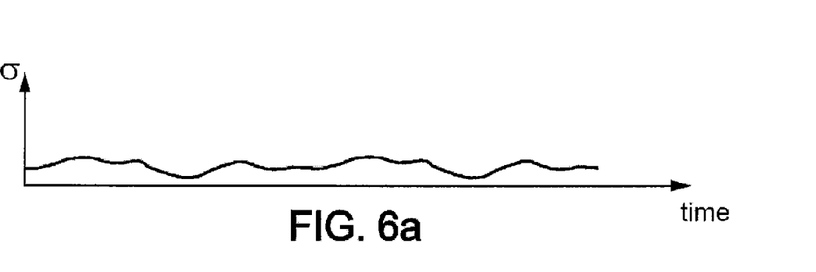
FIGS. 6a and 6b are graphs illustrating the evolution in electrical conductivity over time during drilling in two respective bone structures of different qualities.
Figure 6B:
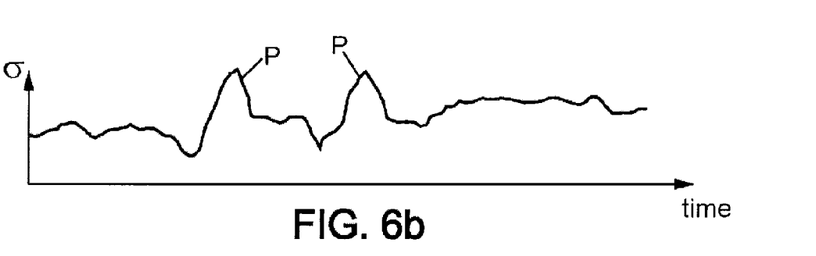

For example, in FIGS. 6a and 6b, each of the conductivity values representative of the local quality of the bone structure 2 measured during the determined period of time is measured and indicated instantaneously as well as being summed with the other values measured during the determined period of time in order to allow mathematical integration of the conductivity values. The mathematical integration representative of the entire drilling can then give an indication of the overall quality of the drilling, taking into account gaps found in the path of the measuring instrument 5 and inhomogeneities encountered. In particular, it can be arranged so that the anchorage of an implant will be considered of better quality in the drilling where the measurement of the conductivity values is represented in FIG. 6a than in the drilling where the measurement of the conductivity values is represented in FIG. 6b. Indeed, the latter measurement shows two peaks P corresponding to gaps in the bone structure 2.

Thus the determination system 1 allows precise, local and instantaneous measurement that provides immediate information during surgery concerning the quality of the bone structure where the surgeon is directly working. As has been shown, this system can easily be integrated into a surgical instrument. The quality of the bone structure can therefore be determined without increasing the length of the surgery.

The information obtained concerning the quality of the bone structure 2 allows the surgeon to make informed treatment decisions during and after the surgery and helps him decide what is best for his patient. For example, during the surgery, the surgeon can optimize:
- the type of implant to be used (expansion screw), its dimensions (smaller or larger diameter), hook placement, etc.,
- the number of implants: adding a level (an additional vertebra), decision not to place a screw in an overly fragile bone, etc.,
- supplemental treatment: use or non-use of bone cement, etc.,
- implant placement: optimal implant placement by choosing the exact site of the implantation because the local solidity of the bone is known (e.g. bicortical sacral), etc.,
- the type of maneuver to be performed to adjust the applied peroperative mechanical stresses to the bone quality, particularly maneuvers to correct deformation or spondylolisthesis, which if too strong could cause peroperative detachment of implants, etc.

The determination system of the invention also applies to continuous measurement of bone remodeling after fracture or after fusion.

Figure 7:
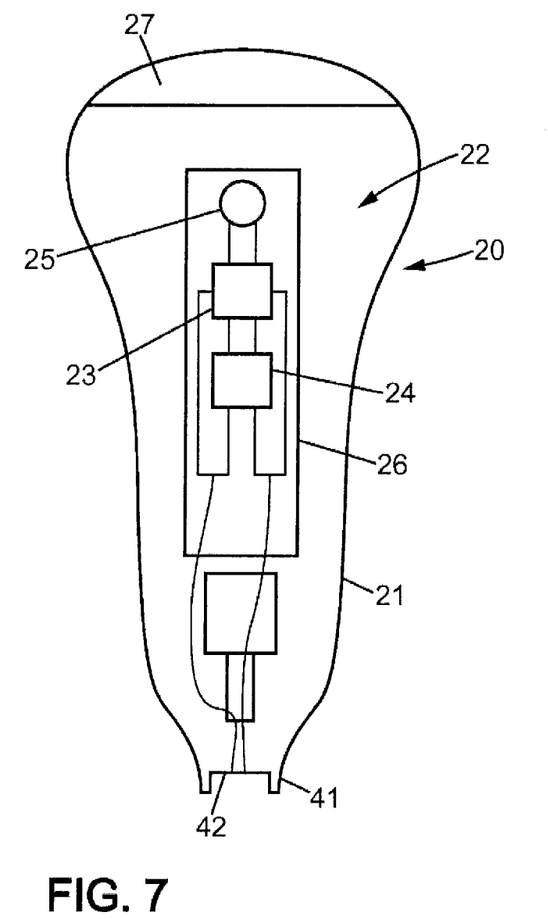
FIG. 7 is a representation of a measuring instrument used in a system for determining the quality of a bone structure according to a second embodiment of the invention.

For this aspect, a second embodiment of the system for determining the quality of the bone structure is described in relation to FIG. 7. This second embodiment has the same main components as the first embodiment, only differing in that the handle 21 and the body 40 are attached to one another in a detachable manner. Refer to the above description for more details on the components.

The body 40 is for example in the form of a screw, particularly a pedicle screw, intended for implantation in a bone structure 2. The body is made of a biocompatible material, implantable in the bone structure 2, and has an outside surface adapted to allow anchoring the body in the bone structure 2. In the particular case of a screw, the outside surface is threaded. As was the case for the body 10 described above, the body 40 bears first 11 and second 12 electrodes arranged in a manner analogous to what was described above, without being limited to this arrangement.

The handle 21 has an end 41 adapted for detachably engaging with the body 40 and causing it to rotate so that it penetrates the bone structure. In particular, a housing 42, for example polygonal in shape, adapted for receiving a head 43 that is integral to the body 40, for example of a polygonal shape analogous to that of the housing 42, can be provided. As a variant, the handle 42 could be shaped like a screwdriver with a tip adapted to engage with a slit in the head 43.

The end of the handle 21 then comprises electrical connection means, such as electrical contacts, arranged to come into contact with the first 11 and second 12 electrodes when the body 40 is attached to the handle, in order to electrically connect the first 11 and second 12 electrodes to the electric generator 23 and to the measuring device 24.

The determination system according to the second embodiment can advantageously be used in a bone structure consolidation system in which the electric generator 23 is adapted for applying an electrical signal to stimulate bone growth. This arrangement allows measuring bone growth progress by measuring the evolution in the quality of the bone structure and using this information as input to the electric generator 23 in its capacity as electrical stimulator, in order to optimize the electrical stimulation signal emitted as a function of the value obtained for the bone structure quality.

Optimization of the electrical stimulation signal can be done manually, by the surgeon to whom the quality of the bone structure has been communicated by any appropriate means. As a variant, the optimization of the electrical stimulation signal can be done automatically. To do so, it can then be arranged so that the central control unit 30, by means of the processing device 28, is adapted to control the electric generator 23 as a function of the signal representative of the quality of the bone structure 2, particularly the porosity of the bone structure. The bone growth stimulation treatments can thus be adjusted automatically by means of a feedback loop.

The use of such a feedback loop for controlling the electric generator and the measuring device is not limited to this application in bone structure consolidation by electrical stimulation.

It could additionally be arranged so that the system for determining the quality of the bone structure is combined, in another consolidation system, with any electrical stimulation device other than the one consisting of the electric generator 23 and the first 11 and second 12 electrodes. For this purpose, it is sufficient to use any appropriate electrical stimulation device which allows applying electrical bone growth stimulation to the bone structure. Preferably, the electrical stimulation can be regulated in order to adjust it, manually or automatically, according to the signal representative of the bone structure quality.

The bone structure consolidation system is not restricted to utilizing the system for determining bone quality according to the second embodiment. In particular, the system for determining bone quality according to the first embodiment or any other system for determining bone quality operating according to the determination principle described above could be utilized in the bone structure consolidation system.

For example, in the context of a bone fusion application but also in any other application, because the measurement of electrical conductivity indicates the quality of the surrounding bone structure, the first 11 and second 12 electrodes, the voltage or current generator 23, the measuring device 24, the power supply device 25, as well as a remote communication interface with the processing device 28, could be integrated into an implant (screw, plate, pin, cage, lead, or other) placed inside the body of the patient, under the skin. During the patient healing period, the physician can thus remotely read the measured electrical conductivity value and know the status of the bone consolidation and the anchorage.

The first 11 and second 12 electrodes can then be carried by a body of a biocompatible material, implantable in the bone structure, while the voltage or current generator 23, the measuring device 24, the power supply device 25, and the remote communication interface are placed in a casing also made of a biocompatible material, implantable inside the body of the patient. Fixation means ensure the fixation of the casing and the body near the bone structure 2, directly to the bone structure and/or to the tissues surrounding the bone structure.

In addition or as an alternative to electrical stimulation, the bone structure consolidation system comprises a fixation device adapted for immobilizing the bone structure so as to allow bone reconstruction. Measuring the bone structure quality then allows monitoring the progress of the bone reconstruction around the fixation device.

Figure 8A:
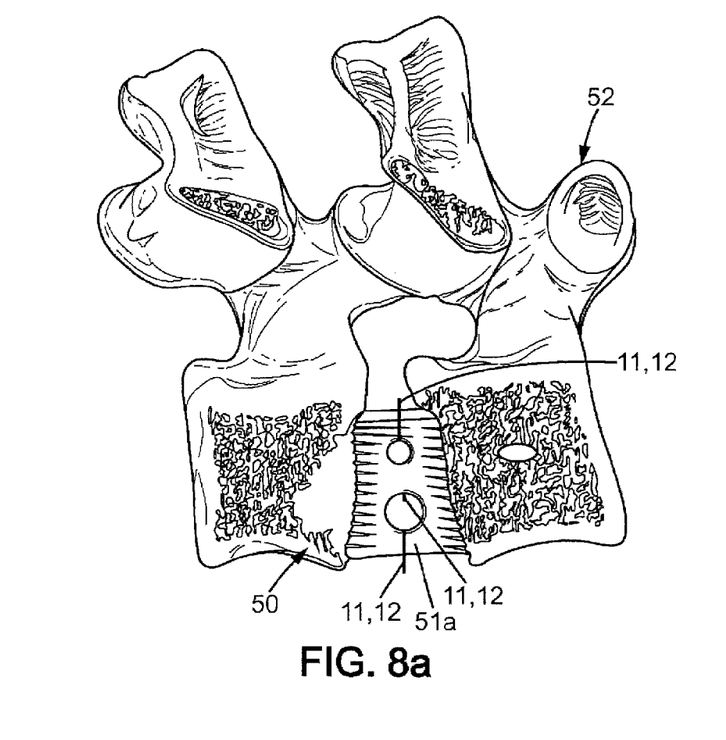
FIGS. 8a and 8b are schematic representations of a first embodiment of a system for consolidating a bone structure which makes use of a system for determining the quality of a bone structure, and a fixation device in the form of a cage for intervertebral fusion, the entire determination system being implantable.
Figure 8B:
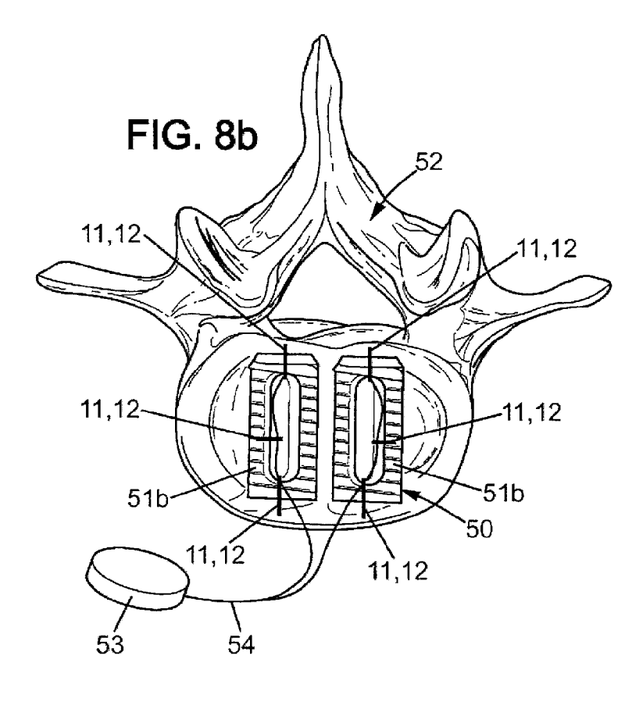

In FIGS. 8a and 8b, a first embodiment is schematically represented of a bone structure consolidation system utilizing a system for determining the quality of a bone structure, and a fixation device.

The fixation device is in the form of an intervertebral fusion cage 50 with several associated electrodes which can form selectively the first 11 and second 12 electrodes of the system for determining the quality of the bone structure. In particular, the cage 50 can comprise a threaded portion, in the shape of a truncated cone 51a in FIG. 8a and cylindrical 51b in FIG. 8b, implanted in a vertebra 52. The first 11 and second 12 electrodes are integrated with the threaded portion 51a such that their contact surface is in contact with an area located between two vertebrae 52 where a bone graft has been placed in order to obtain a solid fusion of the two vertebrae 52. The threaded portion 51a thus forms a body to which is connected a casing 53 that encloses at least the voltage or current generator 23, the measuring device 24, and the power supply device 25.

The casing 53 is internal or implantable, meaning placed under the skin of the patient by being attached, for example, to the soft tissue near the vertebra 52. The casing 53 is then connected to the first 11 and second 12 electrodes by a wired connection 54 and comprises a communication interface, preferable remote, for communicating with the processing device 28 if the latter is not integrated into the casing 53 or with a central control unit.

However, it is possible for the casing 53 to be external, meaning placed outside the patient and connected by a wired or other connection to the first 11 and second 12 electrodes. The casing 53 can then communicate with the processing device 28 if the latter is not integrated into the casing 53 or with a central control unit by a wired or remote communication interface.

Figure 9:
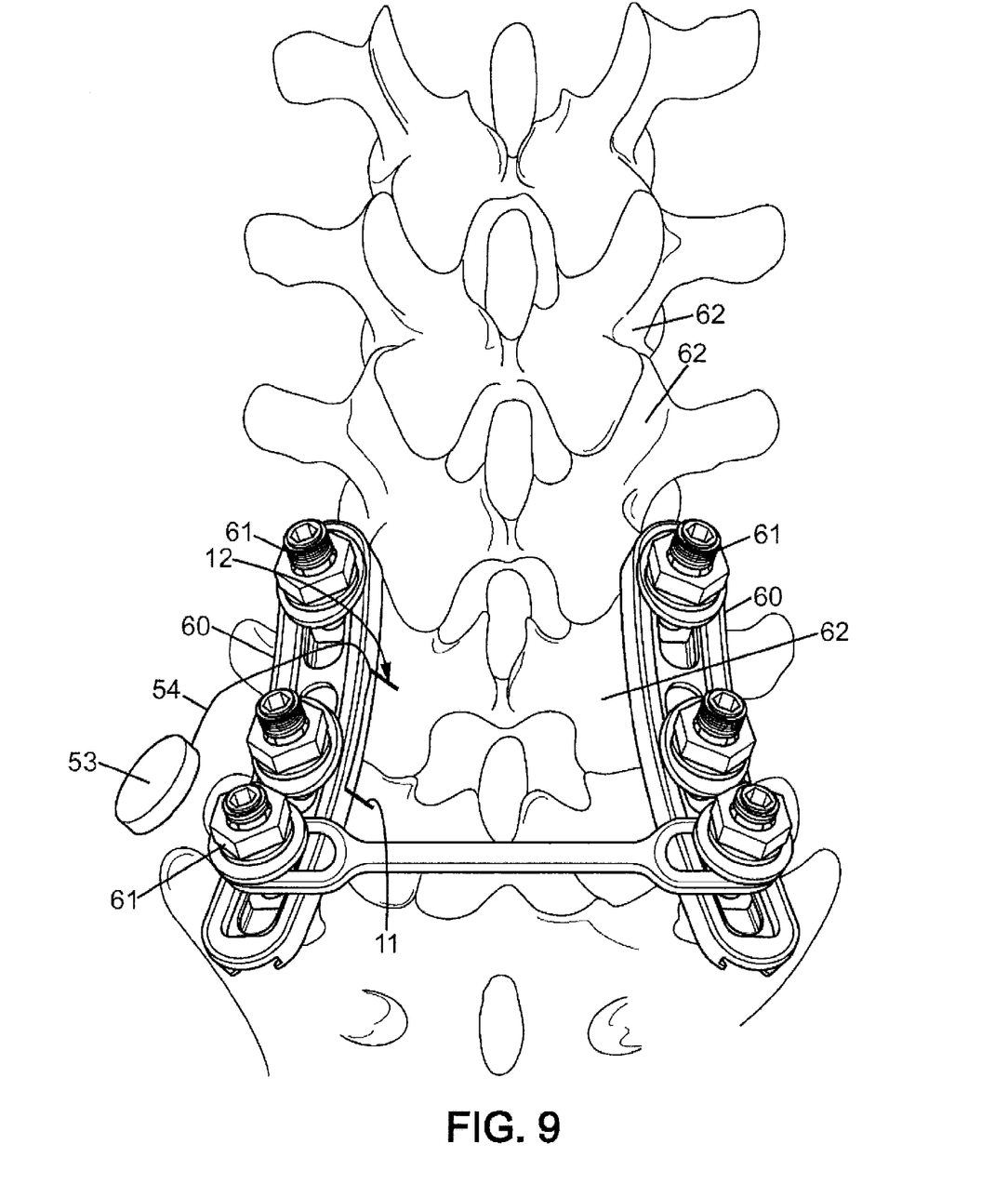
FIG. 9 is a schematic representation of a system for consolidating a bone structure according to a variant of the first embodiment of FIGS. 8a and 8b, the fixation device being in the form of a plate for osteosynthesis.

As a variant represented schematically in FIG. 9, the consolidation system comprises a fixation device in the form of two osteosynthesis plates 60 fixed, parallel to each other, to several vertebrae 62 by means of fixation screws 61. The first 11 and second 12 electrodes are integrated with the fixation device, for example into one of the osteosynthesis plates 60, into each of the osteosynthesis plates 60, or into the fixation screws 61. The casing 53, internal or external, is connected to the first 11 and second 12 electrodes by a wired connection 54.

Advantageously, the attachment device can be adapted to apply a regulated mechanical load to the bone structure, so as to be able to adjust the mechanical load on the bone structure as a function of the signal representative of the bone structure quality.

Indeed, according to Wolff's law, optimal bone consolidation (from a mechanical point of view) is obtained when the bone is subjected during its reconstruction to mechanical strains which are neither too weak (mechanical strains that are too weak do not stimulate bone growth) nor too strong (mechanical strains that are too strong can tear the bone fibers which are still fragile during reconstruction).

As indicated above, the adjustment can be done manually by the surgeon or automatically by means of a feedback loop where the processing device controls the fixation device as a function of the signal representing the quality of the bone structure.

In particular, the fixation device can have a variable geometry which allows varying the mechanical load on the bone structure. For example, the fixation device can comprise at least two fixation elements implantable in the bone structure at a distance from each other, and a connecting element which connects the fixation elements together, said connecting element having an adjustable rigidity.

The connecting element can comprise a flexible portion which gives a certain flexibility to the connection between the fixation elements, and a piezoelectric actuator arranged to adjust the rigidity of the elastic portion. For example, the connecting element can comprise a compressed spring in which the compression can be adjusted by the action of the piezoelectric actuator activated by an energy source.

Figure 10:
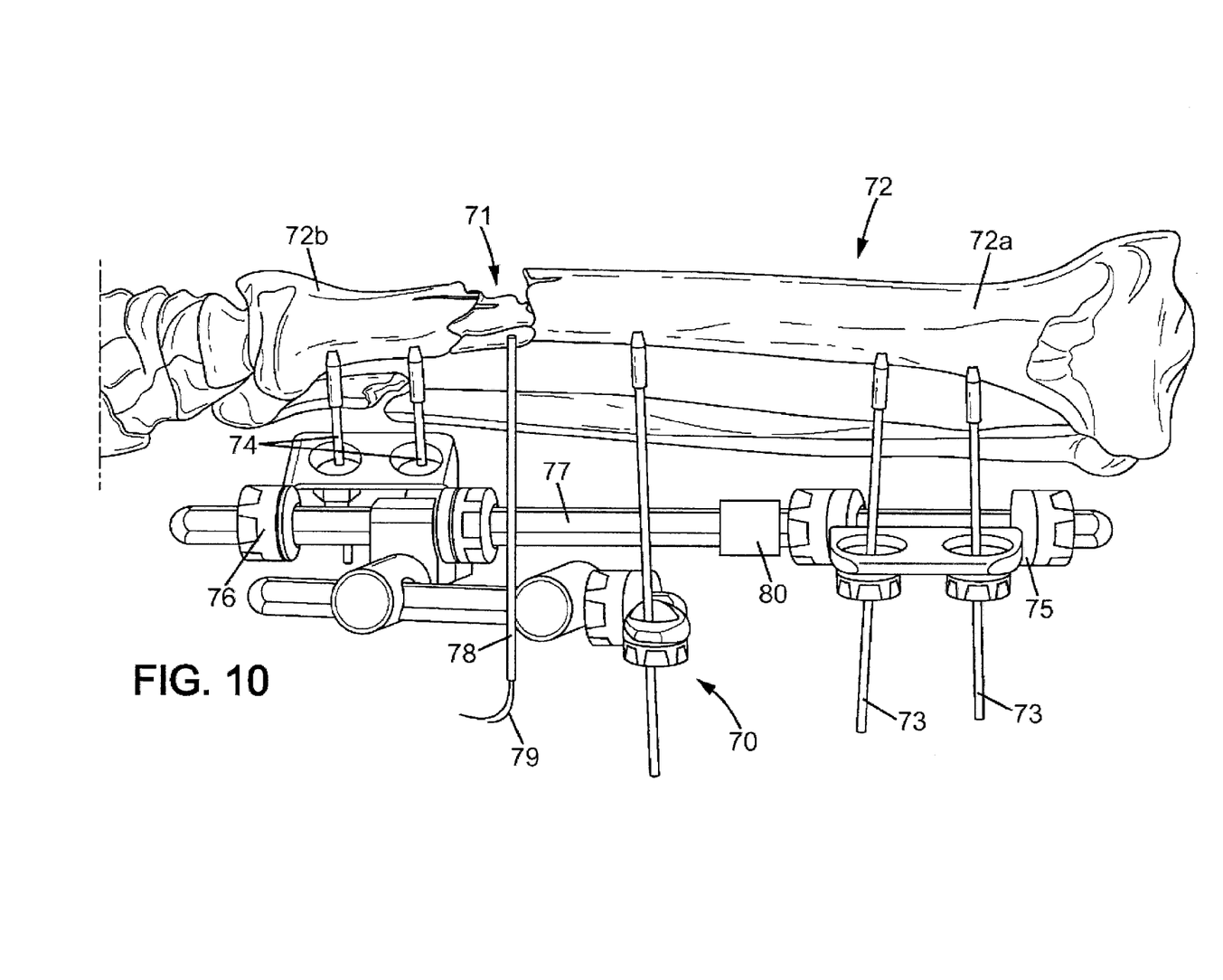
FIG. 10 is a schematic representation of a second embodiment of a system for consolidating a bone structure, which makes use of a system for determining the quality of a bone structure and a fixation device in the form of a device with external fixators.

For example, FIG. 10 illustrates a second embodiment of a system for consolidating a bone structure 72, utilizing a fixation device in the form of an orthopedic device with "external fixators" 70, which allows consolidation of bone fractures while providing a mechanical connection by an external element which connects pins, as fixation elements, implanted on each side of a fracture line, and which extends outside the body of the patient.

In FIG. 10, the bone structure 72, here a tibia, has a first portion 72a and a second portion 72b on each side of a fracture 71. The orthopedic device with "external fixators" 70 comprises a first set of pins 73 inserted into the first portion 72a of the tibia 72, and a second set of pins 74 inserted into the second portion 72b of the tibia 72. The pins 73 in the first set are supported in an adjustable manner by a first carrier 75 and the pins 74 of the second set are supported in an adjustable manner by a second carrier 76. The first 75 and second 76 carriers, located outside the patient, are slidingly mounted on a bar 77, generally parallel to the tibia 72, in order to be able to vary the distance between them.

A measurement pin 78, constituting the body of the system for determining the quality of the bone structure and on which are placed the first 11 and second 12 electrodes, extends from outside the patient to the fracture 71 such that the contact surfaces of the first 11 and second 12 electrodes are in contact with the bone structure at the fracture 71. The first 11 and second 12 electrodes are connected to the electric generator 23, to the measuring device 24, and to the processing device 28 in any appropriate manner, for example by a wired connection 79.

Depending on the quality of the bone structure as determined by the determination system, the distance between the first 75 and second 76 carriers can be adjusted, and the mechanical loads on the bone structure adjusted. This adjustment can be done manually, with the surgeon directly actuating adjustment means, such as dial knobs, provided on the first 75 and second 76 carriers, or automatically, with actuators actuating the adjustment means.

In addition or as an alternative to adjusting the first 75 and second 76 carriers, it is possible for the bar 77 to have an elastic portion 80 in which the rigidity can be adjusted manually or automatically according to the measured quality of the bone structure. Integration of the determination of bone structure quality with such a device with external fixators allows measuring the progress of the bone growth and adjusting the rigidity of the mechanical connection element between the pins 73, 74 of the first and second sets in order to optimize the quality and rapidity of the fusion.

The fixation device may be an orthopedic device with "internal fixators", or an arthrodesis implant, which allows consolidation of bone fractures or arthrodesis, which is surgery in which a joint is replaced by fusion, generally using a bone graft. A mechanical connection by an internal connecting element, for example in the form of a plate or a rod of metal or polymer, is established between screws acting as fixation elements, implanted on each side of the fracture line or the fused joint.

Integrating the determination of the bone structure quality with such a device with internal fixators allows measuring the progress of bone growth, allowing the surgeon, after surgery, to:

optimize consolidation treatments: corset/additional stabilization, external fixators, adjustment (by a minor percutaneous operation under local anesthesia, by remote commands acting on the implant, or in a completely automated manner) of the implant rigidity, stimulation of bone growth, medications, etc., optimize treatment decisions: more surgery depending on the quality of the postoperative anchorage in situ, treatment for pain associated with pseudoarthrosis, etc., follow-up the patient and provide optimal recommendations for bone reconstruction (reeducation, movements to be avoided, etc.).

It should be noted that the determination system described above, although of particular interest in peroperative and postoperative applications in vivo, because they give instant results on the bone structure quality, can also be applied to a bone sample in vitro in order to determine its quality instantaneously, with no other actions. To do this it is sufficient to place the bone sample, collected by biopsy for example, in a conducting solution, particularly normal saline solution, apply the first 11 and second 12 electrodes of known geometry, measure the conductance, and deduce the bone structure quality as described above.

The invention claimed is:

1. A consolidation system for a bone structure of a subject, comprising:

a system for determining a quality of the bone structure, particularly a porosity of the bone structure, said system comprising:

a body presenting an outside surface, at least one first electrode having a first contact surface arranged on the outside surface of the body so as to come into contact with the bone structure;

at least one second electrode having a second contact surface arranged on the outside surface of the body so as to come into contact with the bone structure at a distance from the first electrode;

an electric generator adapted for applying an electric current between the contact surfaces of the first and second electrodes for a determined period of time, said electric current having a known characteristic chosen from among a voltage and an intensity which is known, a measuring device configured to continuously measure over the determined period of time a measured characteristic chosen from among the other of the voltage and the intensity of the electric current passing through the bone structure between the contact surfaces of the first and second electrodes, and a processing device configured to continuously determine over the determined period of time an electrical magnitude representative of a capacity of the bone structure for allowing a passage of the electric current between the contact surfaces of the first and second electrodes, based on the known characteristic and on the measured characteristic, and for continuously delivering over the determined period of time a signal representative of the quality of the bone structure, particularly of the porosity of the bone structure, between the contact surfaces of the first and second electrodes, based on the determined electrical magnitude, wherein the processing device is configured to continuously calculate a value for the electrical magnitude during the determined period of time, and for continuously associating during the determined period of time the value calculated for the electrical magnitude with a value for the quality of the bone structure, particularly the porosity of the bone structure; and a fixation device configured to immobilize the bone structure so as to allow bone reconstruction, the fixation device being configured to apply an adjustable mechanical load to the bone structure, in a manner that adjusts the mechanical load on the bone structure as a function of the signal representative of the quality of the bone structure, particularly of the porosity of the bone structure, wherein the fixation device comprises at least two fixation elements which can be implanted in the bone structure at a distance from one another, and a connecting element which connects the fixation elements, said connecting element having an adjustable rigidity.

2. The system according to claim 1, wherein the electric generator is configured to apply the electric current in the form of at least one electric pulse.

3. The system according to claim 1, wherein the processing device is configured to store a transfer function relating each of the values in a range of values for the electrical magnitude to a value in a range of values for the quality of the bone structure, particularly for the porosity of the bone structure.

4. The system according claim 1, wherein the processing device is configured to establish a first ratio between the known characteristic and the measured characteristic, and for determining the electrical magnitude based on said first ratio.

5. The system according to claim 4, wherein the electrical magnitude is chosen from among the conductivity and the resistivity of the bone structure between the contact surfaces of the first and second electrodes, the processing device being configured to:
   determine a distance between the contact surfaces of the first and second electrodes,
   determine dimensions of the contact surfaces of the first and second electrodes with the bone structure,
   establish a second ratio between said distance and said dimensions, and
   calculate the electrical magnitude based on the first and second ratios.

6. The system according to claim 5, wherein the processing device is configured to store the distance between the contact surfaces of the first and second electrodes, and the dimensions of the contact surfaces of the first and second electrodes with the bone structure.

7. The system according to claim 1, wherein the contact surface of at least one of the first and second electrodes has a dimension greater than 400 μm.

8. The system according to claim 1, wherein the processing device is configured to store a set of values for the electrical magnitude over the determined period of time.

9. The system according to claim 1, wherein the body extends along a central axis to a distal end, with at least one of the first and second electrodes extending parallel to the central axis, the contact surface of said electrode being level with the outside surface of the body at the distal end.

10. The system according to claim 1, wherein at least one of the first and second electrodes extends inside the body to a free end presenting the contact surface, said body comprising a layer of insulating material surrounding said electrode such that only said contact surface is level with the outside surface of the body.

11. The system according to claim 1, comprising a casing attached to the body and a power supply device supplying electrical energy to at least the electric generator and the measuring device, said casing being configured to receive at least the electric generator, the measuring device, and the power supply device.

12. The system according to claim 11, wherein the casing forms a handle from which the body extends.

13. The system according to claim 11, wherein the casing and the body are attached together in a detachable manner, the body being made of a biocompatible material which can be implanted in the bone structure, the outside surface of the body being configured to allow anchoring the body in the bone structure, the casing comprising means for electrically connecting the electric generator and the measuring device to the first and second electrodes.

14. The system according to claim 11, wherein the casing and the body are made of a biocompatible material, implantable inside the subject.

15. The system according to claim 1, further comprising an electrical stimulation device configured to apply an electric bone growth stimulation to the bone structure, the electrical stimulation device being configured to apply an adjustable electrical stimulation to the bone structure, so as to adjust the electrical stimulation on the bone structure as a function of the signal representative of the quality of the bone structure, particularly of the porosity of the bone structure.

16. The system according to claim 15, wherein the processing device is configured to control the stimulation device as a function of the signal representative of the quality of the bone structure.

17. The system according to claim 1, wherein the stimulation device is composed of the electric generator and the first and second electrodes.

18. The consolidation system according to claim 1, wherein the processing device is configured to control the fixation device as a function of the signal representative of the quality of the bone structure.

19. The consolidation system according to claim 1, wherein the connecting element comprises an elastic member exerting stress on the fixation elements, and a piezoelectric actuator arranged for adjusting the stress on the elastic member.

* * * * *